US00PP15171P2

(12) United States Plant Patent
Olesen et al.

(10) Patent No.: US PP15,171 P2
(45) Date of Patent: Sep. 21, 2004

(54) COMPACT FLORIBUNDA ROSA PLANT NAMED 'POULAC015'

(50) Latin Name: *Rosa hybrida*
Varietal Denomination: POULac015

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/719,751

(22) Filed: Nov. 21, 2003

(51) Int. Cl.[7] ..... A01H 5/00
(52) U.S. Cl. ..... Plt./150
(58) Field of Search ..... Plt./150

*Primary Examiner*—Anne Marie Grunberg
*Assistant Examiner*—S B McCormick-Ewoldt

(57) ABSTRACT

A new compact floribunda rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULac015'.

SUMMARY OF THE INVENTION

The present invention constitutes a new and distinct variety of compact floribunda rose plant which originated from a controlled crossing between 'KORstoffein', described and illustrated in U.S. Plant Pat. No. 11,242 issued on Feb. 22, 2000 and an unnamed plant. The two parents were crossed and the resulting seeds were planted in a controlled environment. The new variety is named 'POULac015'.

The new rose may be distinguished from its seed parent, 'KORstoffein', by the following combination of characteristics:

1. The seed parent has 25–30 petals, while 'POULac015' has 65.
2. The upper sides of the petals are Yellow-Orange Group 19C except the innermost petals are Yellow-Orange Group 21C, while 'POULac015' is The new variety may be distinguished from its pollen parent, an unnamed seedling, created by the same inventors, by the following combination of characteristics:

1. While the pollen parent has more than 25 petals, 'POULac015' has between 15 and 25 petals.
2. The flower color of pollen parent is dark red, while 'POULac015' flower color is medium pink.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULac015' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac015' was selected by the inventors as a single plant from the progeny of the hybridization in 1998.

Asexual reproduction of 'POULac015' by cuttings and traditional budding was first done by L. Pernille and Mogens N. Olesen in their nursery in Fredensborg, Denmark in Spring 1999. This initial and other subsequent propagations conducted in controlled environments have demonstrated that the characteristics of 'POULac015' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac015'. Specifically illustrated in THE DRAWING:

FIG. 1.1; Open flower viewed from above, and open flower viewed from the side showing sepals and peduncle;

FIG. 1.2; Flower bud, partially opened bud, and open;

FIG. 1.3; Flower petals, detached;

FIG. 1.4; Sepals, receptacle, and pedicel;

FIG. 1.5; Mature leaf, juvenile leaves exhibiting anthocyanin;

FIG. 1.6; Bare stem exhibiting thorns.

DETAILED DESCRIPTION OF THE VARIETY

The following is a description of 'POULac015', as observed in its growth in glasshouses in Burlington, Canada. Plants are grown in 15 cm pots and are 10 weeks of age. Color references are made using The Royal Horticultural Society (London, England) Colour Chart, 1995, except where common terms of color are used.

For a comparison, several physical characteristics of the rose variety 'POULac001', a rose variety from the same inventors described and illustrated in U.S. Plant Pat. No. 13,272 and issued on Nov. 26, 2002 are compared to 'POULac015' in Chart 1.

CHART 1

| | 'POULac015' | 'POULac001' |
|---|---|---|
| General Tonality | Red-Purple Group 63B to 57C. | Red Group 55C. |
| Petalage | 65. | 25. |
| Bloom diameter | 50 mm. | 80 to 90 mm. |

Parents:

*Female.*—'KORstoffein'.

*Male.*—Unnamed plant.

FLOWER AND FLOWER BUD

Blooming habit: Continuous.

Flower bud:

*Size.*—Upon opening, 17 mm in length from base of receptacle to end of bud.

*Bud form.*—Globular.

*Bud color.*—As sepals unfold, Red-Purple Group 58A to 58B. Red-Purple Group 57B to 57C at ¼ opening.

*Sepals.*—Green Group 137B. Medium foliaceous appendages on three of the five sepals. Surfaces of sepals slightly pubescent. Stipitate glands are scant. Shape: Sepal apex is cirrhose. Foliaceous appendages cause general sepal shape to broaden at the apex on 3 of the 5 sepals. Base is flat at union with peduncle. Size: 31 mm (l)×9 mm (w).

*Receptacle.*—Surface: Smooth and glabrous. Shape: Urn-shaped. Size: 5 mm (h)×6 mm (w). Color: Yellow-Green Group 144A.

*Peduncle.*—Surface: Smooth and glabrous. Strength: Strong.

*Borne.*—Singularly.

*Anthocyanin.*—None observed.

Flower bloom:

*Fragrance.*—Light rose scent.

*Duration.*—As a pot plant, flowers last from 10 to 13 days. Petals fall cleanly away from plant.

*Size.*—Average flower diameter is 50 mm when open.

*Form.*—General form. Shape of flower when viewed from the side: Upon opening, upper part: Flat. Upon opening, lower part: Flattened convex. Open flower, upper part: Convex. Open flower, lower part: Very concave.

*Petalage.*—65 petals on average.

Color:

*Upon opening, petals.*—Outermost petals: Outer Side: Red-Purple Group 57B. Inner Side: Red-Purple Group 57B. Innermost petals: Outer Side: Red-Purple Group 57B. Inner Side: Red-Purple Group 57B.

*Upon opening, basal petal spots.*—Outermost petals: Outer Side: Yellow Group 5C. Inner Side: Yellow Group 5B. Innermost petals: Outer Side: Yellow Group 5C. Inner Side: Yellow Group 5B.

*After opening, petals.*—Outermost petals: Outer Side: Red-Purple Group 63B with variegated intonations of White Group 155B. Inner Side: Red-Purple Group 63B. Innermost petals: Outer Side: Red-Purple Group 63B with variegated intonations of White Group 155B. Inner Side: Red-Purple Group 63B.

*After opening, basal petal spots.*—Outermost petals: Outer Side: White Group 155B. Inner Side: White Group 155B. Innermost petals: Outer Side: White Group 155B. Inner Side: White Group 155B.

General tonality: On open flower Red-Purple Group 63B to 57C. No change in the general tonality at the end of the $5^{th}$ day. Afterwards, general tonality is Red-Purple Group 63C.

Petals:

*Petal reflex.*—Strongly.

*Petal edge.*—Entire with point in center of margin.

*Shape.*—Apex: Round. Base: Round.

*Petaloids.*—Quantity: 10 to 20. Size: 21 mm long; 24 mm wide. Shape: Ovoid to irregular with curvatures.

*Thickness.*—Thick.

*Arrangement.*—Not formal.

*Texture.*—Smooth.

Reproductive organs:

*Pistils.*—Length: 6 mm long. Quantity: 30 (actual count.).

*Pollen.*—None observed.

*Anthers.*—Size: 2 mm long. Color: Greyed-Yellow Group 160B. Quantity: 47 (actual count.).

*Filaments.*—Color: Yellow Group 40 with intonations of Red-Purple Group 58C. Length: 5 mm.

*Stigmas.*—Superior in location to anthers. Color: Greyed-Yellow Group 162D.

*Styles.*—Color: Yellow Group 4D.

*Seed formation.*—Not observed.

PLANT

Plant growth: Vigorous, compact, upright to bushy. When grown as a 15 cm pot plant, the average height of the plant itself is 20 cm and the average width is 18 cm.

Stems:

*Color.*—Young wood: Yellow-Green Group 146A. Older wood: Yellow-Green Group 146A.

*Thorns.*—None observed.

*Stem size.*—Average length: 17 mm. Average diameter: 3 mm.

*Surface.*—Young wood: Smooth. Older wood: Smooth.

Plant foliage: Normal number of leaflets on leaves in middle of the stem: 5 leaflets.

*Leaf size.*—56 mm (l)×mm (w).

*Quantity.*—1 leaf per 5 cm on average.

*Color.*—Upper Leaf Surface: Yellow-Green Group 146A to 147A. Lower Leaf Surface: Yellow-Green Group 138B. Juvenile foliage: Upper Leaf Surface: Yellow-Green Group 144A. Lower Leaf Surface: Yellow-Green Group 144A. Anthocyanin: Location: Underside and leaf margins.

Plant leaves and leaflets:

*Stipules.*—Size: 5 mm. Presence of stipitate glands: Medium. Anthocyanin: None observed.

*Petiole.*—Length: 18 mm. Color: None. Underneath: Thorns and stipitate glands observed.

*Rachis.*—Size: 30 mm in length. Underneath: Thorns and stipitate glands observed. Anthocyanin: None.

*Leaflet.*—Edge: Serrated. Shape: Generally broad based to ovate. Base: Round. Apex: Round. Texture: Smooth and moderately glossy. Arrangement: Odd pinnate. Venation: Reticulate.

Disease resistance: Average resistance to mildew, black spot, and Botrytis under normal growing conditions in Burlington, Canada, and Fredensborg, Denmark.

We claim:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

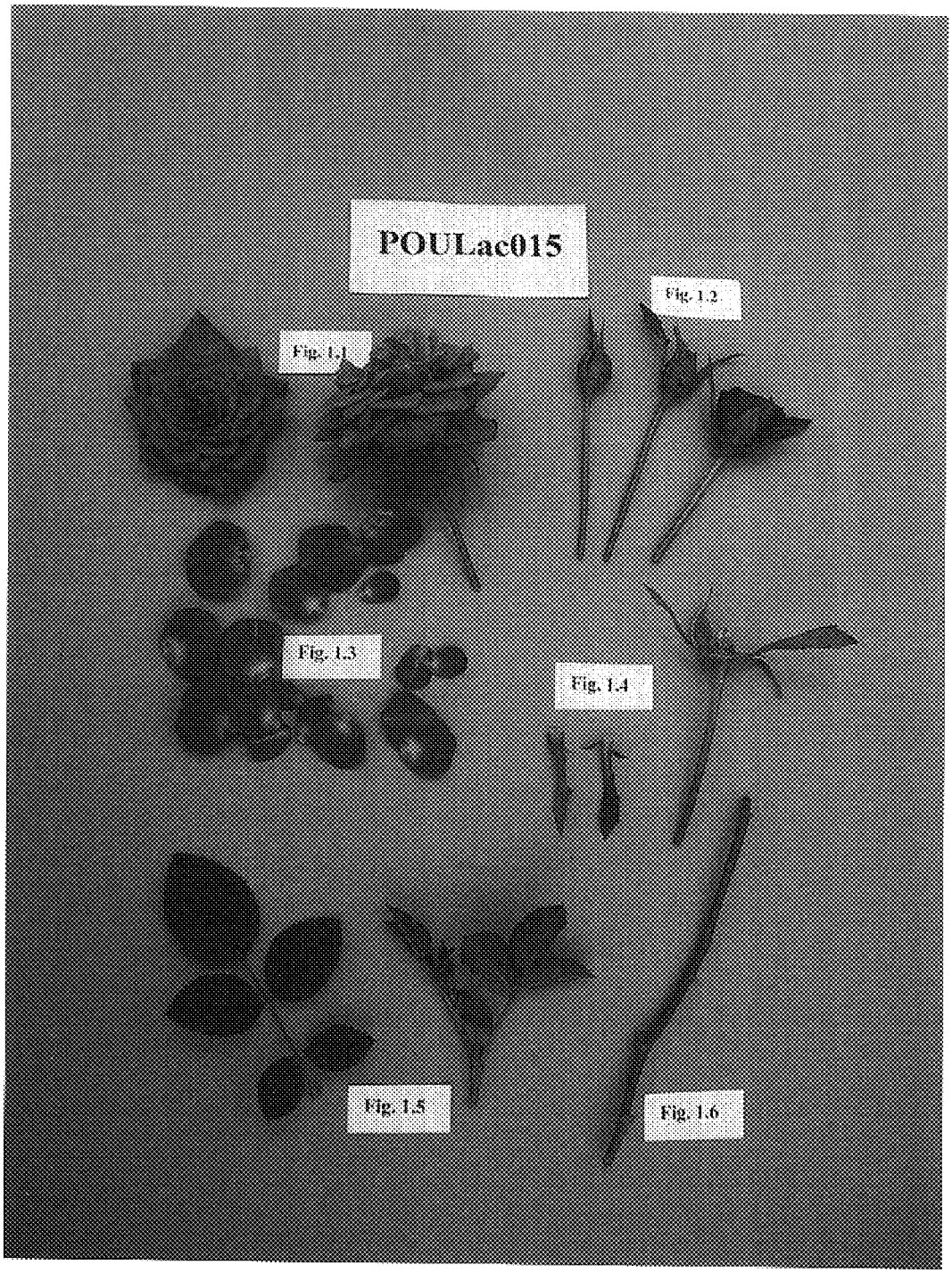
POULac015
Fig. 1.1
Fig. 1.2
Fig. 1.3
Fig. 1.4
Fig. 1.5
Fig. 1.6